(12) United States Patent
Ikeda et al.

(10) Patent No.: US 6,605,717 B2
(45) Date of Patent: Aug. 12, 2003

(54) OPTICALLY ACTIVE EPOXY COMPOUND

(75) Inventors: Hisao Ikeda, Chiba (JP); Motohiko Hidaka, Chiba (JP); Atsumi Aoki, Yamaguchi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/118,260

(22) Filed: Apr. 9, 2002

(65) Prior Publication Data

US 2002/0111485 A1 Aug. 15, 2002

Related U.S. Application Data

(63) Continuation of application No. 09/622,895, filed as application No. PCT/JP99/00931 on Feb. 26, 1999, now Pat. No. 6,444,814.

(30) Foreign Application Priority Data

Mar. 2, 1998 (JP) ............................................. 10-49664

(51) Int. Cl.[7] ...................... C07D 251/10; C07D 251/32
(52) U.S. Cl. ........................................................ 544/192
(58) Field of Search .......................................... 544/192

(56) References Cited

U.S. PATENT DOCUMENTS

| | | | |
|---|---|---|---|
| 5,892,065 | A | 4/1999 | Tsukamoto et al. |
| 6,111,104 | A | 8/2000 | Ikeda et al. |
| 6,124,454 | A | 9/2000 | Ikeda et al. |
| 6,177,541 | B1 | 1/2001 | Ikeda et al. |

FOREIGN PATENT DOCUMENTS

| DE | 29 07 349 | 8/1980 |
|---|---|---|
| JP | WO01/14288 A1 | 3/2001 |

OTHER PUBLICATIONS

A Hempel, et al., Journal of Medicinal Chemistry, vol. 32, 648–651 pp., "Crystallographic Resolution and Crystal and Molecular Structures of Stereoisomers of 1,3,5–Triglycidyl–S–Triazinetrione," 1989.

V. Vargha, et al., Die Angewandle Makromolekulare Chemie, vol. 228, No. 3962, 25–40 pp., "Triglycidyl Isocyanurate Isomers," 1995.

L. N. Mander, Wiley–Vch, 7–8 pp., "Stereoselective Synthese," 1998.

B. Testa, Grundlagen der Organischen Stereochemie, 162–167 pp., "Physikalische Methoden Zur Unterscheidung Von Stereoisomeren," 1983.

V. Vargha, et al., Journal of Thermal Analysis, vol. 36, 1819–1830 pp., "Thermal Behaviour of Triglycidyl–Isocyanurate TGIC in the Presence and in the Absence of Polyester," 1990.

JP02–040373 Abstract Only (1990).
JP55–118484 Abstract Only (Corresponds to DE 29 53 300) (1980).
DE 29 53 300 Abstract Only (1980).

*Primary Examiner*—Taofiq Solola
(74) *Attorney, Agent, or Firm*—Oblon, Spivak, McClelland, Maier & Neustadt, P.C.

(57) ABSTRACT

Optically active β-type tris-(2,3-epoxypropyl)-isocyanurate is obtained by a method of reacting isocyanuric acid with an optically active epihalohydrin, or a method of optically resolving a racemic modification of tris-(2,3-epoxypropyl)-isocyanurate by using an amylose or cellulose derivative. It is a method for producing a high melting point type tris-(2, 3-epoxypropyl)-isocyanurate obtained by mixing two enantiomers of optically active β-type tris-(2,3-epoxypropyl)-isocyanurate.

12 Claims, No Drawings

US 6,605,717 B2

OPTICALLY ACTIVE EPOXY COMPOUND

This application is a continuation of application Ser. No. 09/622,895, filed on Aug. 31, 2000, now U.S. Pat. No. 6,444,814, which was originally filed as International Application No. PCT/JP99/00931, filed on Feb. 26, 1999.

TECHNICAL FIELD

The present invention relates to optically active β-type tris-(2,3-epoxypropyl)-isocyanurate which is an optically active epoxy compound useful as a raw material for e.g. an optical resolution agent, a high polymer catalyst or a nonlinear material such as a nonlinear optical material, or as a crosslinking agent for a compound or a polymer reactive to an epoxy group, a method for producing it, and a method for producing a high melting point type tris-(2,3-epoxypropyl)-isocyanurate obtained by mixing two enantiomers of the optically active β-type tris-(2,3-epoxypropyl)-isocyanurate thus produced, useful as a high polymer material to be used for the field of electricity and electronic industry materials, or as a crosslinking agent for different compounds or for a reactive high polymer.

BACKGROUND ART

To obtain an optically active epoxy compound, a method by asymmetric epoxidation of an olefin has conventionally been known. However, a special and expensive catalyst may be required in this method, or no epoxy compound having a high optical purity tends to be obtained in this method when it is attempted to derive a multifunctional epoxy compound. On the other hand, e.g. an asymmetric resolution method has been known wherein a racemic modification is resolved kinetically by e.g. an enzyme. In this method, it is troublesome to select an enzyme and its conditions, as it is a kinetic resolution method, there is a limit to the optical purity of the compound to be obtained, and no epoxy compound having a high optical purity tends to be obtained when it is attempted to drive a multifunctional epoxy compound, similarly to the above asymmetric epoxidation. From such reasons, no method has been known to produce a multifunctional epoxy compound such as (2R,2'R,2"R)-tris-(2,3-epoxypropyl)-isocyanurate or (2S,2'S,2"S)-tris-(2,3-epoxypropyl)-isocyanurate with a high optical purity. At the same time, no method has been known to optically resolve tris-(2,3-epoxypropyl)-isocyanurate.

Tris-(2,3-epoxypropyl)-isocyanurate has conventionally been known, however, no resolution method nor synthesis method has been known with respect to (2R,2'R,2"R)-tris-(2,3-epoxypropyl)-isocyanurate and (2S,2'S,2"S)-tris-(2,3-epoxypropyl)-isocyanurate, and accordingly, no example has been reported which discloses these substances themselves which are optically active substances.

A tris-(2,3-epoxypropyl)-isocyanurate has three asymmetric carbon atoms. A racemic mixture of (2R,2'R,2"R)-tris-(2,3-epoxypropyl)-isocyanurate and (2S,2'S,2"S)-tris-(2,3-epoxypropyl)-isocyanurate, of which the three asymmetric carbon atoms are coordinate, is commonly called β-type, and is known to provide a crystal having a high melting point of a level of 150° C. This is because a pair of these two enantiomers forms a molecular lattice having six strong hydrogen bonds, and this molecular lattice forms a crystal lattice having high-level hydrogen bonds with other molecular lattices.

On the other hand, a mixture of (2R,2R,2S)-tris-(2,3-epoxypropyl)-isocyanurate and (2S,2S,2R)-tris-(2,3-epoxypropyl)-isocyanurate, of which only one of the three asymmetric carbon atoms has different optical anisotropy, is commonly called α-type, and provides only a low melting point of a level of 100° C. as it does not have a crystal structure as mentioned above.

Since a high melting point type tris-(2,3-epoxypropyl)-isocyanurate not only has a high melting point but has an extremely low solubility in various solvents as compared with e.g. α-type one, when it is used in a form of a one-pack type reactive mixture as a crosslinking agent for different compounds or for a reactive high polymer, the reaction does not proceed during storage until forcible curing under heating. Accordingly, it is used widely in the field of e.g. electricity and electronic industry materials. The method for producing this high melting point type tris-(2,3-epoxypropyl)-isocyanurate is described in e.g. Journal of Thermal Analysis, Vol. 36 (1990) p1819 or Collected papers of High Polymers, Vol. 47, No. 3 (1990) p169, however, there is a drawback such that chlorous impurities derived from decomposed products or epichlorohydrin used as a material are likely to be contained. Further, by the above method, α-type tris-(2,3-epoxypropyl)-isocyanurate as an impurity is likely to be incorporated, and accordingly, it is necessary to make a sacrifice of yield to increase the purity of the high melting point type tris-(2,3-epoxypropyl)-isocyanurate. As the proportion of α-type to β-type as high melting point type, present in the tris-(2,3-epoxypropyl)-isocyanurate obtained by a conventional method, is originally 3:1, the above method is extremely inefficient industrially.

DISCLOSURE OF THE INVENTION

It is to provide (2R,2'R,2"R)-tris-(2,3-epoxypropyl)-isocyanurate and (2S,2'S,2"S)-tris-(2,3-epoxypropyl)-isocyanurate, as optically active β-type tris-(2,3-epoxypropyl)-isocyanurate which is an optically active epoxy compound useful as a high polymer material for e.g. an optical resolution agent or a nonlinear material such as a nonlinear optical material, or as a crosslinking agent for a compound or a high polymer reactive with an epoxy group, a method for efficiently producing it with a high optical purity, and a method for efficiently producing a high melting point type tris-(2,3-epoxypropyl)-isocyanurate with a high purity.

The first aspect of the present invention resides in (2R,2'R,2"R)-tris-(2,3-epoxypropyl)-isocyanurate, The second aspect of the present invention resides in (2S,2'S,2"S)-tris-(2,3-epoxypropyl)-isocyanurate, The third aspect of the present invention resides in a method for producing optically active β-type tris-(2,3-epoxypropyl)-isocyanurate, which comprises reacting isocyanuric acid with an optically active epihalohydrin, The fourth aspect of the present invention resides in the method for producing optically active β-type tris-(2,3-epoxypropyl)-isocyanurate according to the above third aspect, which comprises reacting isocyanuric acid with an optically active epihalohydrin by using, as a catalyst, at least one compound selected from the group consisting of a tertiary amine, a quaternary ammonium salt, a tri-substituted phosphine and a quaternary phosphonium salt, to form a 2-hydroxy-3-halopropyl ester of isocyanuric acid, and adding an alkali metal hydroxide or an alkali metal alcoholate to the obtained 2-hydroxy-3-halopropyl ester of isocyanuric acid, The fifth aspect of the present invention resides in the method for producing optically active βtype tris-(2,3-epoxypropyl)-isocyanurate according to the above third or fourth aspect, wherein 1 mol of isocyanuric acid and from 3 to 60 mol of the optically active epihalohydrin are reacted, The sixth aspect of the present invention resides in the method for producing optically active β-type tris-(2,3-epoxypropyl)-isocyanurate according to any one of the above third to fifth aspects, wherein the water content in the reaction mixed liquid is brought to be less than 1% when 1 mol of isocyanuric acid and the optically active epihalohydrin are reacted, The seventh aspect of the present invention resides in the method for producing optically active β-type tris-(2,3-epoxypropyl)-isocyanurate according to any one of the above third to sixth aspects, which comprises, after the formation of the 2-hydroxy-3-halopropyl ester of isocyanuric acid, recovering the optically active epihalohydrin used in an excessive amount by a distillation method, adding a solvent for dilution, and adding an alkali metal hydroxide or an alkali metal alcoholate, The eighth aspect of the present invention resides in the method for producing optically active β-type tris-(2,3-epoxypropyl)-isocyanurate according to any one of the above third to seventh aspects, which comprises, after the formation of the 2-hydroxy-3-halopropyl ester of isocyanuric acid, recovering the optically active epihalohydrin used in an excessive amount by a distillation method, adding for dilution a racemic epihalohydrin or an organic solvent which has a solubility of at most 5% in water, in an amount of at least 1 part by weight based on 1 part by weight of the 2-hydroxy-3-halopropyl ester of isocyanuric acid, and adding an alkali metal hydroxide under reflux while removing water, The ninth aspect of the present invention resides in the method for producing optically active β-type tris-(2,3-epoxypropyl)-isocyanurate according to any one of the above third to eighth aspects, wherein the optically active β-type tris-(2,3-epoxypropyl)-isocyanurate is (2R,2'R,2"R)-tris-(2,3-epoxypropyl)-isocyanurate, The tenth aspect of the present invention resides in the method for producing optically active β-type tris-(2,3-epoxypropyl)-isocyanurate according to any one of the above third to eighth aspects, wherein the optically active β-type tris-(2,3-epoxypropyl)-isocyanurate is (2S,2'S,2"S)-tris-(2,3-epoxypropyl)-isocyanurate, The eleventh aspect of the present invention resides in a method for producing optically active β-type tris-(2,3-epoxypropyl)-isocyanurate, which comprises optically resolving a racemic modification of tris-(2,3-epoxypropyl)-isocyanurate by using an amylose or cellulose derivative, and The twelfth aspect of the present invention resides in a method for producing a high melting point type tris-(2,3-epoxypropyl)-isocyanurate with a high purity, which comprises mixing the (2R,2'R,2"R)-tris-(2,3-epoxypropyl)-isocyanurate and the (2S,2'S,2"S)-tris-(2,3-epoxypropyl)-isocyanurate which are optically active β-type tris-(2,3-epoxypropyl)-isocyanurate obtained by the method as defined in the above third to eleventh aspects, with a molar ratio of 1:1.

BEST MODE FOR CARRYING OUT THE INVENTION

In the present invention, optically active β-type tris-(2,3-epoxypropyl)-isocyanurate is (2R,2'R,2"R)-tris-(2,3-epoxypropyl)-isocyanurate and (2S,2'S,2"S)-tris-(2,3-epoxypropyl)-isocyanurate.

(2R,2'R,2"R)-tris-(2,3-epoxypropyl)-isocyanurate has the following structural formula (1):

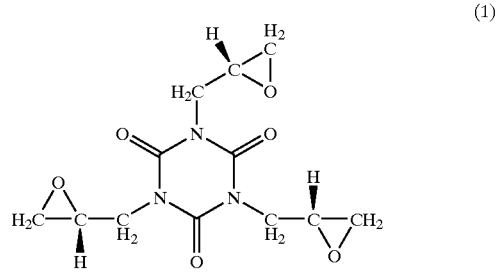

Likewise, (2S,2'S,2"S)-tris-(2,3-epoxypropyl)-isocyanurate has the following structural formula (2):

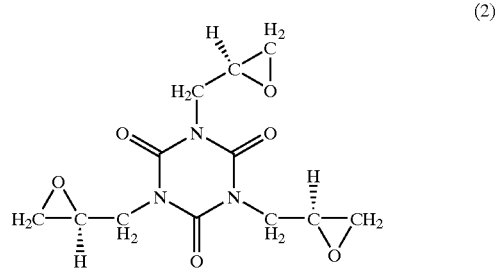

In the present invention, an optically active β-type tris-(2,3-epoxypropyl)-isocyanurate may be produced by a method using as materials isocyanuric acid and an optically active epihalohydrin. For example, a method may be mentioned wherein a trialkali metal isocyanurate obtained by reacting isocyanuric acid with an alkali metal hydroxide in an amount three times the isocyanuric acid, and an optically active epihalohydrin, are heated in a solvent, to carry out removal of alkali metal chloride. However, it may be produced preferably by the following method.

Namely, isocyanuric acid and an optically active epihalohydrin are reacted to obtain a 2-hydroxy-3-halopropyl ester of isocyanuric acid, and an alkali metal hydroxide or an alkali metal alcoholate is added thereto.

In the above reaction of isocyanuric acid with an optically active epihalohydrin, the optically active epihalohydrin is added in an amount of from 3 to 60 mol, preferably from 6 to 60 mol, more preferably from 10 to 30 mol, based on 1 mol of isocyanuric acid. Further, as a catalyst, at least one compound selected from the group consisting of a tertiary amine, a quaternary ammonium salt, a tri-substituted phosphine and a quaternary phosphonium salt, is used, and its amount is from 0.001 to 0.1 mol, particularly preferably from 0.01 to 0.05 mol, based on 1 mol is isocyanuric acid.

The reaction of isocyanuric acid with an optically active epihalohydrin is carried out in such conditions that the water content in the entire reaction mixed liquid is less than 1%, preferably at most 0.1%, more preferably at most 100 ppm, and the reaction temperature is from 40 to 115° C., preferably from 60 to 100° C.

Optically active β-type tris-(2,3-epoxypropyl)-isocyanurate may be produced with a high efficiency, and a side reaction will be suppressed, by adding an alkali metal hydroxide or an alkali metal alcoholate in an amount of preferably from 3.0 to 6.0 mol, more preferably from 3.0 to 4.0 mol, to 1 mol of the 2-hydroxy-3-halopropyl ester of isocyanuric acid as an intermediate.

For the above reaction, in addition to an optically active epihalohydrin, another organic solvent may be used. However, it is preferred to use optically active epichlorohydrin alone as a reaction reagent and as a solvent, since the side reaction which will decompose the desired product will be suppressed, and the reaction rate will be increased.

As epichlorohydrin to be used for industrially producing conventional tris-(2,3-epoxypropyl)-isocyanurate is recovered and recycled as mentioned above, water may be mixed therein. Further, as the reaction of addition of epihalohydrin to isocyanuric acid will be accelerated by adding water to the reaction mixed liquid, the reaction is carried out usually by adding water in an amount of from 1 to 5% based on the entire reaction mixed liquid. However, in the reaction of isocyanuric acid with an optically active epihalohydrin of the present invention, it is preferred to suppress the water content in the entire reaction mixed liquid to be less than 1% so as to suppress the racemization of the optically active epihalohydrin.

As the optically active epihalohydrin, R- or S-epichlorohydrin, epibromohydrin, epiiodohydrin may, for example, be mentioned. Since there is a possibility of racemization when the reaction with isocyanuric acid is carried out at a high temperature, it is preferred to add, as a catalyst to carry out the reaction moderately, at least one compound selected from the group consisting of a tertiary amine, a quaternary ammonium salt, a tri-substituted phosphine and a quaternary phosphonium salt. For example, as the tertiary amine, tripropylamine, tributylamine or N,N'-dimetylpiperazine may, for example, be mentioned. Further, as the tri-substituted phosphine, tripropylphosphine, tributylphosphine, triphenylphosphine or tritolylphosphine may, for example, be mentioned. Further, as the quaternary ammonium salt, a tetramethylammonium halide, a tetraethylammonium halide or a tetrabutylammonium halide may, for example, be mentioned, and as said halide, chloride, bromide or iodide may, for example, be mentioned. Still further, as the quaternary phosphonium salt, a tetramethylphosphonium halide, a tetrabutylphosphonium halide, a methyltriphenylphosphonium halide or an ethyltriphenylphosphonium halide may, for example, be mentioned, and as said halide, chloride, bromide or iodide may, for example, be mentioned. Among these compounds, preferred are quaternary ammonium salts and quaternary phosphonium salts, as the reaction will proceed efficiently under milder conditions with less side reaction. More preferred are quaternary ammonium salts, and among them, most preferred is a tetraethylammonium halide, and as said halide, it is preferred to use chloride or bromide, since the side reaction will be more suppressed, and the catalyst will be easily removed by washing with water after the reaction.

Further, as the alkali metal hydroxide or the alkali metal alcoholate to be added so as to arouse dehydrohaloganation from the 2-hydroxy-3-halopropyl ester of isocyanuric acid, for example, as the metal hydroxide, sodium hydroxide, potassium hydroxide or lithium hydroxide may be mentioned, and as the alkali metal alcoholate, sodium methylate, sodium ethylate, potassium methylate or potassium ethylate may be mentioned.

If the alkali metal hydroxide or the alkali metal alcoholate is added directly after the formation of the 2-hydroxy-3-halopropyl ester of isocyanuric acid, the optically active epihalohydrin used in an excessive amount tends to undergo racemization. Accordingly, the optically active epihalohydrin used in an excessive amount may be recovered by a distillation method before the addition of the alkali metal hydroxide or the alkali metal alcoholate, followed by adding a solvent for dilution, and then the alkali metal hydroxide or the alkali metal alcoholate may be added. Preferably, the optically active epihalohydrin used in an excessive amount may be recovered by a distillation method, and instead, a racemic epihalohydrin which is industrially easily available at a low cost or an organic solvent having a solubility of at most 5% in water may be added for dilution in an amount of at least 1 part by weight based on 1 part by weight of the 2-hydroxy-3-halopropyl ester of isocyanuric acid, and then the alkali metal hydroxide may be added under reflux while removing water. The solvent to be used is particularly preferably a racemic epihalohydrin since the decomposition of the reaction product will be reduced.

The reaction of treatment with the alkali metal hydroxide is carried out preferably by dropping from 20 to 60 wt %, preferably from 40 to 55 wt %, of an aqueous alkali metal hydroxide solution under reflux while removing water, at a reaction temperature of as low as possible, preferably from 10 to 80° C., more preferably from 20 to 70° C., and the degree of pressure reduction is adjusted so that the amount of reflux of the racemic epihalohydrin or the organic solvent having a solubility of at most 5% in water will be made large. In the case of dropping from 40 to 55 wt % of an aqueous alkali metal hydroxide solution, the amount of reflux is preferably at least five times the addition amount, since the side reaction to decompose the specified substance tris-(2,3-epoxypropyl)-isocyanurate will be suppressed.

By the above method, (2R,2'R,2"R)-tris-(2,3-epoxypropyl)-isocyanurate and (2S,2'S,2"S)-tris-(2,3-epoxypropyl)-isocyanurate can be efficiently produced with a high optical purity. Further, by purification by recrystallization using a solvent such as methanol, it is possible to produce (2R,2'R,2"R)-tris-(2,3-epoxypropyl)-isocyanurate and (2S,2'S,2"S)-tris-(2,3-epoxypropyl)-isocyanurate with an optical purity of at least 99% ee.

On the other hand, the present inventors have invented also a method for efficiently producing (2R,2'R,2"R)-tris-(2,3-epoxypropyl)-isocyanurate and (2S,2'S,2"S)-tris-(2,3-epoxypropyl)-isocyanurate with a high optical purity, by optical resolution of tris-(2,3-epoxypropyl)-isocyanurate by using an amylose or cellulose derivative.

As the amylose or cellulose derivative to be used in the present invention, a triester derivative or a tricarbamate derivative of amylose or cellulose may be used. Among them, cellulose triphenylcarbamate, cellulose tris-p-tolylcarbamate, cellulose tribenzoate, cellulose triacetate, cellulose tricinnamate, cellulose tris(3,5-dimethylphenylcarbamate), cellulose tris(4-chlorophenylcarbamate), cellulose tris(4-methylbenzoate), amylose tris(3,5-dimethylphenylcarbamate) and amylose tris(1-phenylethylcarbamate) may be mentioned. Among them, particularly preferred is an aromatic type carbamate such as cellulose tris-p-tolylcarbamate, cellulose tris(3,5-dimethylphenylcarbamate), amylose tris(3,5-dimethylphenylcarbamate) or amylose tris(1-phenylethylcarbamate), and the resolution will most efficiently be carried out by amylose tris(3,5-dimethylphenylcarbamate) or amylose tris(1-phenylethylcarbamate).

In the present invention, as the method of optically resolving tris-(2,3-epoxypropyl)-isocyanurate by using the amylose or cellulose derivative, a known method may be used wherein the amylose or cellulose derivative is supported on a silica gel, for example, which is packed in a column, to separate tris-(2,3-epoxypropyl)-isocyanurate by column chromatography. These amylose or cellulose derivative to be used for the optical resolution agent, the column and the like may be used repeatedly, and the optical purity of at least 99%ee and the optical yield of about 100% will be obtained by employing a proper eluent, and accordingly it is an effective production method.

By the above method, (2R,2'R,2"R)-tris-(2,3-epoxypropyl)-isocyanurate and (2S,2'S,2"S)-tris-(2,3-epoxypropyl)-isocyanurate can be produced efficiently with a high optical purity. Further, as a result of studies, the present inventors have found that a high melting point type tris-(2,3-epoxypropyl)-isocyanurate can be produced with a high purity in a high yield, by mixing the enantiomers of high purity thus obtained in a molar ratio of 1:1. It may be obtained, for example, by melt-mixing them at a temperature of at least the melting point of both, for example, at 120° C.

Further, as another method, (2R,2'R,2"R)-tris-(2,3-epoxypropyl)-isocyanurate and (2S,2'S,2"S)-tris-(2,3-epoxypropyl)-isocyanurate are respectively dissolved in a solvent having a high solubility in (2R,2'R,2"R)-tris-(2,3-epoxypropyl)-isocyanurate and (2S,2'S,2"S)-tris-(2,3-epoxypropyl)-isocyanurate and having a low solubility in a high melting point type tris-(2,3-epoxypropyl)-isocyanurate, and the respective solutions are mixed to obtain a high melting point type tris-(2,3-epoxypropyl)-isocyanurate with substantially no α-type tris-(2,3-epoxypropyl)-isocyanurate as an impurity contained therein.

As the solvent, a variety of solvents such as halogen type solvents including dichloromethane, chloroform and trichloroethane, aprotic polar solvents including dimethylformamide, dimethylsulfoxide and dimethylacetamide, nitril type solvents including acetonitrile and adiponitrile, ether type solvents including dioxane and tetrahydrofuran, ketone type solvents including acetone and methyl ethyl ketone, as well as ester type solvents including ethyl acetate and aromatic type solvents including benzene and toluene, may, for example, be used. Among them, preferred is a solvent having a solubility of at least 10% at room temperature in (2R,2'R,2"R)-tris-(2,3-epoxypropyl)-isocyanurate and (2S,2'S,2"S)-tris-(2,3-epoxypropyl)-isocyanurate. The solvent is preferably liquid in the vicinity of 25° C., and has a boiling point of as low as possible, for example, a boiling point of from about 30° C. to about 150° C., since the solvent will hardly remain as an impurity.

With respect to (2R,2'R,2"R)-tris-(2,3-epoxypropyl)-isocyanurate and (2S,2'S,2"S)-tris-(2,3-epoxypropyl)-isocyanurate obtained in the present invention, the compounds themselves may be used as such. Further, they may be cured by using as a curing agent, e.g. a polyvalent active hydrogen compound having reactivity with epoxy, such as an acid anhydride, a polyamine, a polycarboxylic acid, a polyol, a polyphenol or a polymercaptan. In such a case, a Lewis acid such as boron trifluoride or a boron trifluoride complex, a strong acid such as p-toluene sulfonic acid, or a compound to be used commonly as a curing accelerator, such as imidazole, may, for example, be used together, or a Lewis acid such as boron trifluoride or a boron trifluoride complex, imidazole or dicyandiaminde alone may be used as a curing agent for curing. (2R,2'R,2"R)-tris-(2,3-epoxypropyl)-isocyanurate and (2S,2'S,2"S)-tris-(2,3-epoxypropyl)-isocyanurate or cured products thereof, are useful as a stationary phase of an optical resolution agent, as a raw material for high polymer catalysts, or as a nonlinear material such as a nonlinear optical material.

On the other hand, the high melting point type tris-(2,3-epoxypropyl)-isocyanurate also provides a cured product having an excellent heat resistance by the above method, and in addition, it may be used for applications in the field of electricity and electronic industrial materials, as a curing agent for a polyhydric active hydrogen compound having reactivity with epoxy, such as a high polymer having a reactive substituent such as a carboxylic acid. As mentioned above, as the high melting point type tris-(2,3-epoxypropyl)-isocyanurate has a low solubility in a solvent, it has such a characteristic that it can be preserved for a long period of time as a reactive mixed liquid of one-pack type together with a high polymer having a reactive substituent.

EXAMPLE 1

Optical Resolution of tris-(2,3-epoxypropyl)-isocyanurate

As an amylose derivative, amylose tris(1-phenylethylcarbamate) was used. Using a column for optical resolution (commercially available column [CHIRALPAK AS] (manufactured by DAICEL CHEMICAL INDUSTRIES, LTD.), 0.46 cm in diameter×25 cm in length) having amylose tris(1-phenylethylcarbamate) supported on a silica gel having a sililation treatment applied thereto, 10 μl of a 100 ppm solution having an acetonitrile 10 wt % solution of tris-(2,3-epoxypropyl)-isocyanurate (racemic modification) diluted 1000 times in a weight ratio with an eluent, was injected for separation by chromatography, under such conditions that eluent: n-hexone/ethanol (70/30 v/v), column temperature: 40° C., flow rate: 1.0 ml/min., and UV detector: 210 nm. As a result, (2R,2'R,2"R)-tris-(2,3-epoxypropyl)-isocyanurate was isolated at 8.79 minutes, (2R,2R,2S)-tris-(2,3-epoxypropyl)-isocyanurate at 9.37 minutes, (2R,2S,2S)-tris-(2,3-epoxypropyl)-isocyanurate at 10.10 minutes, and (2S,2'S,2"S)-tris-(2,3-epoxypropyl)-isocyanurate at 10.69 minutes.

Here, in the present invention, the optical purity of tris-(2,3-epoxypropyl)-isocyanurate and α-type tris-(2,3-epoxypropyl)-isocyanurate contained as an impurity were determined by using said resolution conditions.

EXAMPLE 2

Optical Resolution of tris-(2,3-epoxypropyl)-isocyanurate)

As an amylose derivative, amylose tris(3,5-dimethylphenylcarbamate) was used. Using a column for optical resolution (commercially available column [CHIRALPAK AD] (manufactured by DAICEL CHEMICAL INDUSTRIES, LTD.), 0.46 cm in diameter×25 cm in length) having amylose tris(3,5-dimethylphenylcarbamate) supported on a silica gel having a sililation treatment applied thereto, 10 μl of a 100 ppm solution having an acetonitrile 10 wt % solution of tris-(2,3-epoxypropyl)-isocyanurate (racemic modification) diluted 1000 times in a weight ratio with an eluent, was injected for separation by chromatography, under such conditions that eluent: n-hexone/ethanol (40/60 v/v), column temperature: 24° C., flow rate: 1.0 ml/min., and UV detector: 210 nm. As a result, (2R,2'R,2"R)-tris-(2,3-epoxypropyl)-isocyanurate was isolated at 11.00 minutes, (2R,2R,2S)-tris-(2,3-epoxypropyl)-isocyanurate at 12.87 minutes, (2R,2S,2S)-tris-(2,3-epoxypropyl)-isocyanurate at 14.20 minutes, and (2S,2'S,2"S)-tris-(2,3-epoxypropyl)-isocyanurate at 16.80 minutes.

EXAMPLE 3

Optical Resolution of tris-(2,3-epoxypropyl)-isocyanurate

As an amylose derivative, amylose tris(1-phenylethylcarbamate) was used. Using an HPLC which has columns for optical resolution connected in series (commercially available columns [CHIRALPAK AS] (manufactured by DAICEL CHEMICAL INDUSTRIES, LTD.)) having amylose tris(1-phenylethylcarbamate) supported on a silica gel having a sililation treatment applied thereto, respectively 1.0 cm in diameter×5 cm in length, and 1.0 cm in diameter and 25 cm in length, 10 µl of an acetonitrile 2 wt % solution of tris-(2,3-epoxypropyl)-isocyanurate (racemic modification) was repeatedly injected under such conditions that eluent: n-hexone/ethanol (70/30 v/v), column temperature: 400° C., flow rate: 1.0 ml/min., and UV detector: 210 nm, whereupon (2R,2'R,2"R)-tris-(2,3-epoxypropyl)-isocyanurate effused at 18.9 minutes and (2S,2'S,2"S)-tris-(2,3-epoxypropyl)-isocyanurate effused at 24.5 minutes were batched off.

The effused solutions were concentrated under reduced pressure to obtain 10.1 mg of (2R,2'R,2"R)-tris-(2,3-epoxypropyl)-isocyanurate (at least 99%ee) and 9.2 mg of (2S,2'S,2"S)-tris-(2,3-epoxypropyl)-isocyanurate (at least 99%ee) respectively as colorless viscous materials.

EXAMPLE 4

Synthesis of (2R,2'R,2"R)-tris-(2,3-epoxypropyl)-isocyanurate

To a flask having a capacity of 3 l and equipped with a stirring apparatus, a thermometer, a continuous dropping apparatus and an apparatus which concentrates azeotropic vapor of water and R-epichlorohydrin having a water content of 2% under reduced pressure and returns R-epichlorohydrin alone to the reaction system, 129 g (1 mol) of isocyanuric acid, 1890 g (20 mol) of R-epichlorohydrin having a water content of 2% and 0.7 g of tetraethylammonium bromide were added, followed by stirring at 90° C. for 10 hours. Then, the pressure in the reaction system was reduced to 50 mmHg, and the total of 320 g (4 mol) of an aqueous sodium hydroxide solution having a concentration of 50 wt % was dropwise added over a period of about 3 hours for reaction, while keeping the temperature in the reaction container to be from 40 to 50° C. During this reaction, water added dropwise and water formed were removed to outside of the system by azeotropy with R-epichlorohydrin.

After the reaction, the inside of the reaction container was cooled to room temperature, and sodium hydroxide used in an excessive amount was neutralized by washing by using a 10% aqueous sodium dihydrogen phosphate solution. Then, salt was removed by washing with water, and R-epichlorohydrin was distilled off under reduced pressure (10 mmHg) at 120° C. to obtain 205 g of (2R,2'R,2"R)-tris-(2,3-epoxypropyl)-isocyanurate. Its epoxy equivalent was 104 g/eq, $[\alpha]_D^{20}$=+15.8° (c=0.5, $H_2O$), and it was a colorless viscous liquid. Further, R-epichlorohydrin distilled off and recovered was confirmed to be substantially racemized (at most 5%ee).

EXAMPLE 5

Synthesis of (2R,2'R,2"R)-tris-(2,3-epoxypropyl)-isocyanurate

To a flask having a capacity of 3 l and equipped with a stirring apparatus, a thermometer, a continuous dropping apparatus and an apparatus which concentrates azeotropic vapor of water and R-epichlorohydrin having a water content of 100 ppm under reduced pressure and returns R-epichlorohydrin alone to the reaction system, 129 g (1 mol) of isocyanuric acid, 1850 g (20 mol) of R-epichlorohydrin and 0.7 g of tetraethylammonium bromide were added, followed by stirring at 90° C. for 10 hours. Then, the pressure in the reaction system was reduced to 50 mmHg, and the total of 280 g (3.5 mol) of an aqueous sodium hydroxide solution having a concentration of 50 wt % was dropwise added over a period of about 3 hours for reaction, while keeping the temperature in the reaction container to be from 40 to 50° C. During this reaction, water added dropwise and water formed were removed to outside of the system by azeotropy with R-epichlorohydrin.

After the reaction, the inside of the reaction container was cooled to room temperature, and sodium hydroxide used in an excessive amount was neutralized by washing by using a 10% aqueous sodium dihydrogen phosphate solution. Then, salt was removed by washing with water, and R-epichlorohydrin was distilled off under reduced pressure (10 mmHg) at 120° C. to obtain 205 g of (2R,2'R,2"R)-tris-(2,3-epoxypropyl)-isocyanurate. Its epoxy equivalent was 103 g/eq, $[\alpha]_D^{20}$=+2.1° (c=0.5, $H_2O$), and it was a colorless viscous liquid. Further, R-epichlorohydrin distilled off and recovered was confirmed to be substantially racemized (at most 5%ee).

(2R,2'R,2"R)-tris-(2,3-epoxypropyl)-isocyanurate thus obtained was put in a flask of 3 l equipped with a stirring apparatus, a thermometer and a reflux condenser, together with 2 l of methanol, followed by stirring at 60° C. for dissolution. Then, the solution was left to stand at room temperature for air cooling to carry out recrystallization. The crystal was subjected to filtration, and methanol adhered to the crystal was removed under reduced pressure (10 mmHg) at 100° C. to obtain 152 g of (2R,2'R,2"R)-tris-(2,3-epoxypropyl)-isocyanurate. Its epoxy equivalent was 99 g/eq, $[\alpha]_D^{20}$+20.73° (c=0.5, $H_2O$), the melting point was from 100.7 to 104.9 ° C., at least 99%ee, and it was a white needle crystal.

EXAMPLE 6

Synthesis of (2S,2'S,2"S)-tris-(2,3-epoxypropyl)-isocyanurate

To a flask having a capacity of 3 l and equipped with a stirring apparatus, a thermometer, a continuous dropping apparatus and an apparatus which concentrates azeotropic vapor of water and S-epichlorohydrin having a water content of 100 ppm under reduced pressure and returns S-epichlorohydrin alone to the reaction system, 129 g (1 mol) of isocyanuric acid, 1850 g (20 mol) of S-epichlorohydrin and 0.7 g of tetraethylammonium bromide were added, followed by stirring at 90° C. for 10 hours. Then, S-epichlorohydrin used in an excessive amount was recovered by distillation at 64° C. under 13 mmHg. S-epichlorohydrin recovered was 1295 g, ee=98.5%.

Then, 1300 g of racemic epichlorohydrin as a solvent was added to the reaction liquid, the pressure in the reaction system was reduced to 50 mmHg, and the total of 280 g (3.5 mol) of an aqueous sodium hydroxide solution having a concentration of 50 wt % was dropwise added over a period of about 3 hours for reaction, while keeping the temperature in the reaction container to be from 40 to 50° C. During this reaction, water added dropwise and water formed were removed to outside of the system by azeotropy with racemic epichlorohydrin.

After the reaction, the inside of the reaction container was cooled to room temperature, and sodium hydroxide used in an excessive amount was neutralized by washing by using a 10% sodium dihydrogen phosphate solution. Then, salt was removed by washing with water, and S-epichlorohydrin was distilled off under reduced pressure (10 mmHg) at 120° C. to obtain 198 g of (2S,2'S,2"S)-tris-(2,3-epoxypropyl)-isocyanurate. Its epoxy equivalent was 103 g/eq, $[\alpha]_D^{20}$=−20.0° (c=0.5, $H_2O$), and it was a white solid.

(2S,2'S,2"S)-tris-(2,3-epoxypropyl)-isocyanurate thus obtained was put in a flask of 3 l equipped with a stirring apparatus, a thermometer and a reflux condenser, together with 2 l of methanol, followed by stirring at 60° C. for dissolution. Then, the solution was left to stand at room temperature for air cooling to carry out recrystallization. The crystal was subjected to filtration, and methanol adhered to the crystal was removed under reduced pressure (10 mmHg) at 100° C. to obtain 145 g of (2S,2'S,2"S)-tris-(2,3-epoxypropyl)-isocyanurate. Its epoxy equivalent was 99 g/eq, $[\alpha]_D^{20}$=−20.82 (c=0.5, $H_2O$), the melting point was from 100.7 to 104.9° C., at least 99%ee, and it was a white needle crystal.

EXAMPLE 7

Synthesis of High Melting Point Type tris-(2,3-epoxypropyl)-isocyanurate

A solution having 5 mg of (2R,2'R,2"R)-tris-(2,3-epoxypropyl)-isocyanurate obtained in Example 3 dissolved in 5 mg of acetonitrile, and a solution having 5 mg of (2S,2'S,2"S)-tris-(2,3-epoxypropyl)-isocyanurate dissolved in 5 mg of acetonitrile, were mixed, and left to stand at 25° C. for at least one day. The crystal thus precipitated was subjected to filtration, and acetonitrile adhered to the crystal was distilled off under reduced pressure to obtain 9.7 mg (yield 97%) of high melting point type tris-(2,3-epoxypropyl)-isocyanurate. It contained at most 0.1% of α-type as an impurity, had a melting point of from 155.2 to 157.1° C., and was a colorless plate crystal.

EXAMPLE 8

Synthesis of High Melting Point Type tris-(2,3-epoxypropyl)-isocyanurate

To a flask in which 5 g of (2R,2'R,2"R)-tris-(2,3-epoxypropyl)-isocyanurate obtained in Example 4 was melted by heating to 150° C., 5 g of (2S,2'S,2"S)-tris-(2,3-epoxypropyl)-isocyanurate obtained in Example 5 melted by heating to 150° C. was introduced and mixed, and left to stand at 25° C. for at least one day, to obtain 10 g (yield 100%) of high melting point type tris-(2,3-epoxypropyl)-isocyanurate. It contained at most 0.1% of α-type as an impurity, had a melting point of from 149.2 to 155.1° C., and was a white crystal.

EXAMPLE 9

To a glass container of 50 mL equipped with a stirring apparatus, 1 g of (2R,2'R,2"R)-tris-(2,3-epoxypropyl)-isocyanurate obtained in Example 5, 1.35 g of phthalic anhydride (commercially available reagent chemical), 0.02 g of benzyltriphenylphosphonium bromide (commercially available reagent) and 10 g of tetrahydrofuran were put, followed by stirring for mixing at 80° C. until a slight increase in viscosity was confirmed. To this mixed liquid, a silica gel having a sililation treatment applied thereto was charged, and tetrahydrofuran was distilled off by an evaporator. Then, the temperature was increased by stages in the evaporator, and finally a treatment was carried out at 150° C. for about 1 hour, and baking was carried out in an oven at 180° C. for 1 hour. This surface-treated silica gel was packed in a stainless column of 1.0 cm in diameter×25 cm in length, and optical resolution of 1,1'-bi-2-naphthol was carried out by using an HPLC, using as an eluent n-hexon/ethanol, at a column temperature of 40° C. at a flow rate of 1.0 ml/min. As a result, R-formation was resolved at 11.5 min., and S-formation at 12.5 min.

COMPARATIVE EXAMPLE 1

Synthesis of High Melting Point Type tris-(2,3-epoxypropyl)-isocyanurate 100 g of tris-(2,3-epoxypropyl)-isocyanurate [commercially available high purity tris-(2,3-epoxypropyl)-isocyanurate, tradename: TEPIC-S, epoxy equivalent: 100 g/eq, manufactured by Nissan Chemical Industries, Ltd.] and 1.5 l of methanol were put in a flask of 2 l equipped with a stirring apparatus, a thermometer and a reflux condenser, followed by stirring at 60° C. for 2 hours, then the insolubles were separated by filtration. The crystal thus obtained was adequately washed with methyl ethyl ketone. The crystal was subjected to filtration, and methyl ethyl ketone adhered to the crystal was removed under reduced pressure (10 mmHg) at 100° C. to obtain 27.3 g (yield 27.3%) of high melting point type tris-(2,3-epoxypropyl)-isocyanurate. It contained 23.5% of α-form as an impurity, had an epoxy equivalent of 99 g/eq and a melting point of from 140.2 to 150.3° C., and was a white crystal.

COMPARATIVE EXAMPLE 2

Synthesis of High Melting Point Type tris-(2,3-epoxypropyl)-isocyanurate 100 g of tris-(2,3-epoxypropyl)-isocyanurate [commercially available high purity tris-(2,3-epoxypropyl)-isocyanurate, tradename: TEPIC-S, epoxy equivalent: 100 g/eq, manufactured by Nissan Chemical Industries, Ltd.] and 1.5 l of methanol were put in a flask of 2 l equipped with a stirring apparatus, a thermometer and a reflux condenser, followed by stirring at 60° C. for 2 hours, then the insolubles were separated by filtration. The crystal thus obtained was adequately washed with methyl ethyl ketone, and recrystallization was carried out once from methyl ethyl ketone. The crystal was finally subjected to filtration, and methyl ethyl ketone adhered to the crystal was removed under reduced pressure (10 mmHg) at 100° C. to obtain 15.2 g (yield 15.2%) of high melting point type tris-(2,3-epoxypropyl)-isocyanurate. It contained 5.7% of α-form as an impurity, had an epoxy equivalent of 99 g/eq and a melting point of from 145.3 to 151.1° C., and was a white crystal.

COMPARATIVE EXAMPLE 3

Synthesis of High Melting Point Type tris-(2,3-epoxypropyl)-isocyanurate 100 g of tris-(2,3-epoxypropyl)-isocyanurate [commercially available high purity tris-(2,3-epoxypropyl)-isocyanurate, tradename: TEPIC-S, epoxy equivalent: 100 g/eq, manufactured by Nissan Chemical Industries, Ltd.] and 1.5 l of methanol were put in a flask of 2 l equipped with a stirring apparatus, a thermometer and a reflux condenser, followed by stirring at 60° C. for 2 hours, then the insolubles were separated by filtration. The crystal thus obtained was adequately washed with methyl ethyl ketone, and recrystallization was carried out twice from methyl ethyl ketone. The crystal was finally subjected to filtration, and methyl ethyl ketone adhered to the crystal was removed under reduced pressure (10 mmHg) at 100° C. to obtain 10.3 g (yield: 10.3%, recovery of high melting point type: 41%) of high melting point type tris-(2,3-epoxypropyl)-isocyanurate. It contained 0.5% of α-form as an impurity, had an epoxy equivalent of 99 g/eq and a melting point of from 150.4 to 152.1° C., and was a white crystal.

Industrial Applicability

With respect to the properties of (2R,2'R,2"R)-tris-(2,3-epoxypropyl)-isocyanurate and (2S,2'S,2"S)-tris-(2,3-epoxypropyl)-isocyanurate which have not conventionally been known, the present invention has found by isolating them and confirming their properties that they are excellent compounds as a curing agent for an optical resolution agent.

Heretofore, no method has been known to optically resolve tris-(2,3-epoxypropyl)-isocyanurate. However, it becomes possible to easily and efficiently obtain (2R,2'R,2"R)-tris-(2,3-epoxypropyl)-isocyanurate and (2S,2'S,2"S)-tris-(2,3-epoxypropyl)-isocyanurate by optical resolution using an amylose or cellulose derivative. In this case, when an amylose or cellulose derivative is supported on an inert carrier, preferably e.g. a silica gel, and packed in a column, followed by elution with a proper solvent, there are such advantages that the optical resolution will be carried out more easily and precisely, and the column will be recycled.

Further, it becomes possible to produce (2R,2'R,2"R)-tris-(2,3-epoxypropyl)-isocyanurate and (2S,2'S,2"S)-tris-(2,3-epoxypropyl)-isocyanurate efficiently with a high optical purity from isocyanuric acid and an optically active epihalohydrin. It is possible to obtain a higher optical purity by controlling e.g. the water content in the system, and it becomes possible to recover the optically active epihalohydrin used in an excessive amount while keeping a high optical purity.

Further, by mixing (2R,2'R,2"R)-tris-(2,3-epoxypropyl)-isocyanurate and (2S,2'S,2"S)-tris-(2,3-epoxypropyl)-isocyanurate obtained by these methods in a ratio of 1:1, it becomes possible to obtain a high melting point type tris-(2,3-epoxypropyl)-isocyanurate, which is of β-type, in a high yield with substantially no α-type tris-(2,3-epoxypropyl)-isocyanurate contained, which is an impurity to be contained in the case of conventional production.

What is claimed is:

1. (2R,2'R,2"R)-tris-(2,3-epoxypropyl)-isocyanurate.
2. (2S,2'S,2"S)-tris-(2,3-epoxypropyl)-isocyanurate.
3. (2R,2'R,2"R)-tris-(2,3-epoxypropyl)-isocyanurate having an optical purity of at least 99% ee.
4. (2S,2'S,2"S)-tris-(2,3-epoxypropyl)-isocyanurate having an optical purity of at least 99% ee.
5. A method for producing a high melting point β-type tris-(2,3-epoxypropyl)-isocyanurate having a high purity, comprising:

mixing in a molar ratio of 1:1 a (2R,2'R,2"R)-tris-(2,3-epoxypropyl)-isocyanurate and a (2S,2'S,2"S)-tris-(2,3-epoxypropyl)-isocyanurate which are optically active β-type tris-(2,3-epoxypropyl)-isocyanurates obtained by reacting isocyanuric acid with an optically active epihalohydrin.

6. The method according to claim 5, wherein said (2R,2'R,2"R)-tris-(2,3-epoxypropyl)-isocyanurate and said (2S,2'S,2"S)-tris-(2,3-epoxypropyl)-isocyanurate are mixed by melt-mixing at a temperature of at least the melting point of both.

7. The method according to claim 5, wherein each of said (2R,2'R,2"-R)-tris-(2,3-epoxypropyl)-isocyanurate and said (2S,2'S,2"S)-tris-(2,3-epoxypropyl)-isocyanurate are dissolved in a solvent which has a higher solubility for said optically active β-type tris-(2,3-epoxypropyl)-isocyanurates than for said high melting point β-type tris-(2,3-epoxypropyl)-isocyanurate, to obtain two solutions; and mixing said two solutions, to obtain said high melting point β-type tris-(2,3-epoxypropyl)-isocyanurate.

8. The method according to claim 5, wherein said high melting point β-type tris-(2,3-epoxypropyl)-isocyanurate comprises substantially no α-type tris-(2,3-epoxypropyl)-isocyanurate.

9. The method according to claim 7, wherein said solvent is selected from the group consisting of a halogen solvent, an aprotic polar solvent, a nitril solvent, an ether solvent, a ketone solvent, an ester solvent, and an aromatic solvent.

10. The method according to claim 7, wherein said solvent dissolves at least 10% of said optically active β-type tris-(2,3-epoxypropyl)-isocyanurates.

11. The method according to claim 7, wherein said solvent is liquid in the vincinity of 25° C.

12. The method according to claim 7, wherein said solvent has a boiling point of from about 30 to about 150° C.

* * * * *